United States Patent [19]

Farge et al.

[11] 4,053,300
[45] Oct. 11, 1977

[54] AGRICULTURAL COMPOSITION INCORPORATING DERIVATIVES OF 7H-INDOLIZINO (7,6,5-DE)-ISOQUINOLINE

[75] Inventors: Daniel Farge, Thiais; Yves LeGoff, Bretigny, Orge; Gilbert Poiget, Thiais, all of France

[73] Assignee: Philagro, Lyon, France

[21] Appl. No.: 704,922

[22] Filed: July 13, 1976

[30] Foreign Application Priority Data

July 15, 1975 France .................. 75.22081

[51] Int. Cl.² .............. C07D 471/16; A01N 9/22
[52] U.S. Cl. .................. 71/94; 260/287 D; 260/288 D; 260/288 CF
[58] Field of Search .............. 260/288 CF; 71/94

[56] References Cited

U.S. PATENT DOCUMENTS 3,946,019   3/1976   Farge et al. ............. 260/288 CF

OTHER PUBLICATIONS

Oppolyzer; Chem. Abs.: vol. 78: 58268v (1972).
Fieser et al., Advanced Organic Chemistry, pp. 620–622 (1961).

*Primary Examiner*—Donald G. Daus
*Assistant Examiner*—Mary C. Vaughn
*Attorney, Agent, or Firm*—Browdy and Neimark

[57] ABSTRACT

A new derivative of 7H-indolizino (7,6,5-de)-isoquinoline of the formula

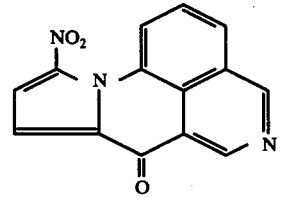

is useful as a bactericide against fire blight.

10 Claims, No Drawings

AGRICULTURAL COMPOSITION INCORPORATING DERIVATIVES OF 7H-INDOLIZINO (7,6,5-DE)-ISOQUINOLINE

The present invention relates to a new derivative of 7H-indolizino-(7,6,5-de)isoquinoline of the formula:

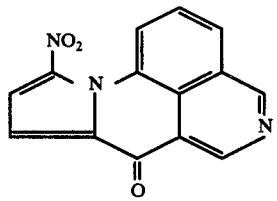
(I)

It also relates to a process for its preparation, and to its application as a bactericidal active material in compositions for agricultural use.

The compound of the formula (I) can be obtained by nitration of a compound of the formula:

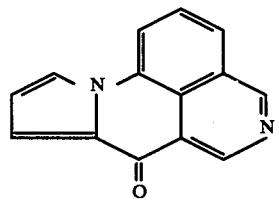
(II)

In general, the reaction is carried out in an organic solvent such as nitromethane, at a temperature of between −10° and −15° C, using, as the nitrating agent, fuming nitric acid in trifluoromethanesulfphonic acid.

The isoquinoline derivative of the formula (II) can be prepared in accordance with one or other of the following methods:

1. By hydrolysis, in a basic medium, of the imine of the formula:

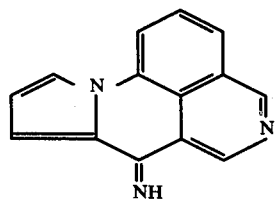
(III)

In general, the reaction is carried out in an organic solvent such as ethanol at the reflux temperature of the reaction mixture.

The imine of the formula (III) can be obtained by reaction of cuprous cyanide with the product of the formula:

(IV)

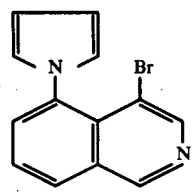

The reaction is generally carried out in a solvent such as N-methylpyrrolidone, at a temperature between 165° and 200° C.

The isoquinoline derivative of the formula (IV) can be obtained by reaction of a tetrahydrofurane derivative of the general formula:

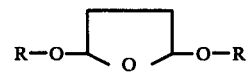
(V)

in which R represents a methyl or ethyl radical, with a 5-amino-isoquinoline derivative of the formula:

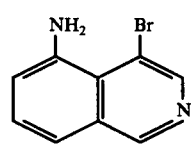
(VI)

In general, the reaction is carried out in an organic solvent such as acetic acid, at the boiling point of the reaction mixture.

The isoquinoline of the formula (VI) can be prepared by the method of EDINGER and BOSSUNG, J. Prakt. Chem., [2]43, 198 (1891).

2. By reaction of a derivative of the general formula (V) with a derivative of 5-amino-isoquinoline of the formula:

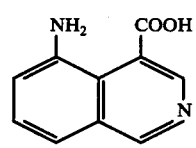
(VII)

The reaction is generally carried out in an organic solvent such as acetic acid, at a temperature of about 90°–100° C.

5-Amino-isoquinoline of the formula (VII) can be prepared by reduction of a 5-nitro-isoquinoline of the formula:

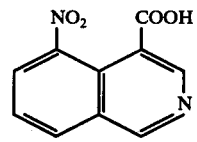
(VIII)

It is particularly advantageous to react ammonium sulphide, prepared in situ, with a product of the formula (VIII) at a temperature of about 90°–100° C.

5-Nitro-isoquinoline of the formula (VIII) can be prepared by nitration of 4-carboxy-isoquinoline.

Advantageously, potassium nitrate in concentrated sulphuric acid is used as the nitrating agent.

4-Carboxy-isoquinoline can be prepared by the method of F. G. TYSON, J. Am. Chem. Soc., 61, 183 (1939).

The examples which follow are given without implying any limitation to illustrate respectively the preparation and the bacteriostatic and bactericidal activity of the compound according to the invention.

EXAMPLE 1

A solution obtained by adding fuming nitric acid ($d = 1.52$) (2.35 cc.) to a solution of trifluoromethanesulphonic acid (17.03 g.) in nitromethane (20.8 cc.) is added over the course of 1 hour to a suspension, which is stirred and kept at between $-10°$ and $-15°$ C, of 7-oxo-7H-indolizino[7,6,5-de] isoquinoline (10 g.) in nitromethane (400 cc.).

Stirring is continued at a temperature of between $-10°$ and $-15°$ C for 1 hour and then at $0° - 2°$ C for 16 hours. The yellow crystals which have appeared are filtered off and washed successively with nitromethane (30 cc.) and with ether (80 cc.). After drying, 10-nitro-7-oxo-7H-indolizino[7,6,5-de]isoquinolinium trifluoromethanesulphonate (8.8 g.) is obtained.

This product is stirred with water (150 cc.) and methylene chloride (300 cc.); the aqueous layer is decanted and then washed with methylene chloride (3 × 150 cc., in succession). The organic extracts are combined and then washed successively with water (100 cc.), 0.1 N sodium hydroxide solution (100 cc.) and water (3 × 100 cc.). The orange-yellow organic solution thus obtained is dried over calcined magnesium sulphate and the solvent is then evaporated under reduced pressure. 10-Nitro-7-oxo-7H-indolizino[7,6,5-de]isoquinoline (4.64 g.) melting at 192° C and then at 201° C is obtained.

After purification by chromatography on silica gel and recrystallisation from acetonitrile (50 parts by volume), the product obtained melts at 194° C and then at 202° C.

7-Oxo-7H-indolizino[7,6,5-de]isoquinoline can be obtained in accordance with one of the following methods:

1. 7-Imino-7H-indolizino[7,6,5-de]isoquinoline (30 g.) and 1 N sodium hydroxide solution (3 cc.) in ethanol (900 cc.) and water (900 cc.) are heated for 18 hours under reflux in a stream of nitrogen. After having evaporated the ethanol under reduced pressure, the crystals which have appeared are filtered off and washed with water (4 × 200 cc.). This gives 7-oxo-7H-indolizino[7,6,5-de]isoquinoline (25.4 g.) melting at 211° C. After recrystallisation from 80% strength ethanol (940 cc.), pure product (11.55 g.) melting at 222° C is obtained.

7-Imino-7H-indolizino[7,6,5-de]isoquinoline can be prepared in the following manner:

Cuprous cyanide (104.9 g.) is added, whilst stirring, to a suspension of 4-bromo-5-(pyrrolyl-1)-isoquinoline (63.64 g.) in N-methylpyrrolidone (160 cc.). The viscous suspension obtained is rapidly heated to 165° C and then gradually to 180° C to effect dissolution. The exothermic reaction which starts near this temperature raises the reaction mixture to 200° C. The reaction mixture is then cooled rapidly and is poured into a 10% strength (weight/volume) aqueous solution of potassium cyanide (3.79 liters), and the whole is stirred for 2 hours. The crystals which have appeared are filtered off, washed with water (5 × 250 cc.), then dried and recystallised from acetonitrile (1,350 cc.). This gives 7-imino-7H-indolizino[7,6,5-de]isoquinoline (28.78 g.) in the form of green-yellow crystals melting at 189° C.

4-Bromo-5-(pyrrolyl-1)-isoquinoline can be prepared in the following manner:

2,5-Dimethoxy-tetrahydrofurane (157 g.) is added, over the course of 7 minutes, to a boiling solution of 5-amino-4-bromo-isoquinoline (242 g.) in acetic acid (1,220 cc.) After cooling, the brown solution obtained is poured into water (2.5 liters) and the mixture is rendered alkaline, to pH 9, by adding concentrated ammonia (11 N) and is stirred for 1 hour. The crystals which have appeared are filtered off, washed with water (5 × 1 liter) and dried. After recrystallisation from ethanol (25 parts (weight/volume)) and decolorising with animal charcoal, 4-bromo-5-(pyrrolyl-1)-isoquinoline (172.5 g.) melting at 180° C is obtained.

The mother liquors, after concentration, yield further 4-bromo-5-(pyrrolyl-1)-isoquinoline (49.18 g.) melting at 171° C.

5-Amino-4-bromo-isoquinoline can be prepared by the method of EDINGER and BOSSUNG, J. Prakt. Chem., [2] 43, 198 (1891).

2. 2,5-Dimethoxy-tetrahydrofurane (63.4 g.) is added to a solution of 5-amino-4-carboxy-isoquinoline (82 g.) in acetic acid (410 cc.). The solution obtained is stirred and gradually heated to 90°–95° C over the course of 15 minutes. The limpid brown solution is cooled to a temperature of about 20° C and is then poured into distilled water (2 liters). The brown precipitate which forms is extracted with chloroform (2.5 liters in total). The organic extracts are washed successively with 2N sodium hydroxide solution (2 × 1 liter) and distilled water (3 × 0.5 liter). After drying over sodium sulphate, and evaporating the solvent under reduced pressure, crude 7-oxo-7H-indolizino[7,6,5-de]isoquinoline (70 g.) melting at 216° C and then at 226° C is obtained.

After recrystallisation from 80% strength ethanol (37 parts), the pure product melts at 222° C, then resolidifies and thereafter melts at 231° C.

The 5-amino-4-carboxy-isoquinoline used as the starting material can be prepared in the following manner:

A solution of 4-carboxy-5-nitro-isoquinoline (144.1 g.) in ammonia (11N) (364 cc.) and water (304 cc.) is saturated with a stream of hydrogen sulphide at 25°–35° C and is then kept at 90° – 100° C for 1 hour 40 minutes. The precipitate of sulphur which forms is filtered off hot and the filtrate is then cooled to about 20° C and treated with decolorising charcoal.

The limpid red filtrate obtained after filtration is acidified by adding acetic acid (49.5 cc.) and is then concentrated to a volume of 100 cc. under reduced pressure (1 mm Hg). The concentrate, kept at about 5° C for 16 hours, sets to a crystalline mass. The yellow crystals are filtered off and washed successively with iced water (3 × 50 cc.), ethanol (3 × 50 cc.) and ether (2 × 100 cc.). After drying, 5-amino-4-carboxy-isoquinoline (82.9 g.) is obtained in the form of yellow crystals melting at 232° C.

The 4-carboxy-5-nitro-isoquinoline starting material can be prepared in the following manner:

A nitrating mixture obtained by dissolving potassium nitrate (94 g.) in concentrated sulphuric acid ($d = 1.83$) (750 cc.) is added dropwise, over the course of 1 hour, to a solution of 4-carboxy-isoquinoline (146.8 g.) in concentrated sulphuric acid ($d = 1.83$) (880 cc.). The solution obtained is kept at a temperature of about 20° C for 16 hours and is then poured onto ice (18 kg.). Ammonia (11 N) (5.5 liters) is added gradually, whilst stirring and keeping the temperature of the mixture at between 15° and 20° C. The yellow precipitate which has appeared is filtered off, washed with water (800 cc. in total) and then dried. 4-Carboxy-5-nitro-isoquinoline (144 g.) melting at 285° is thus obtained.

The 4-carboxy-isoquinoline used as the starting material can be prepared according to the method of F. C. TYSON, J. Am. Chem. Soc., 61, 183 (1939).

EXAMPLE 2

In Vitro Test of the Bacteriostatic Activity

To a series of test tubes containing a defined volume of a culture medium (tryptycase soy broth) is added 1/9 of of this volume of a series of dilutions (in geometrical progression) of a solution of the product to be studied.

The tubes are inoculated with a suitable inoculum (0.05 cc.), namely a culture of the test germ in a liquid medium, which has been incubated for a defined time at the optimum temperature and been diluted as appropriate with a medium of the same composition.

After inoculation, the tubes are placed in an oven for 24 hours at 24° C.

The minimum bacteriostatic concentration which inhibits the development of the various aerobic bacteria is that of the last tube in which the development of the germ is inhibited.

| Germ | Minimum bacteriostatic concentration, µg/cc. |
| --- | --- |
| Corynebacterium fasciens | 2 |
| Corynebacterium michiganense | 0.5 |
| Pseudomonas syringae | 1 |
| Pseudomonas morsprunorum | 0.5 |
| Pseudomonas persicae | 0.5 |
| Xanthomonas juglandis | 4 |
| Xanthomonas phaseoli | 8 |
| Erwinia chrysanthemi | 0.03 |
| Erwinia carotovora | 0.06 |
| Agrobacterium tumefasciens | 2 |

EXAMPLE 3

In Vitro Test of the Bactericidal Activity

A series of tubes identical to those of the preceding test is inoculated with a culture (0.15 ml.) of Erwinia chrysanthemi diluted with a medium of the same composition.

After inoculation, the tubes are placed in an oven at 24° C.

After various times of contact, a 2nd series of tubes containing the culture medium (10 cc.) and some of the contents (0.1 cc.) of the tubes of the 1st series, then a 3rd series of tubes containing 0.1 cc of the content of the tubes of the 2nd series, and culture medium (10 cc.), are made up.

These tubes are incubated at 24° C for 48 hours.

For each period of contact, the concentration of the last tube of the 2nd and 3rd series which does not show development of the test germ and which does not contain the product at a bacteriostatic concentration makes it possible to determine the concentration of the corresponding tube of the 1st series which causes the death of all the germs, that is to say the minimym bactericidal concentration.

| contact time (hours) | Minimum bactericidal concentration, µg/cc. |
| --- | --- |
| 1 | 4 |
| 4 | 1 |
| 24 | 1 |

EXAMPLE 4

In Vivo Test of Persistence on Beans

Bean plants are treated with a range of concentrations of suspensions of the product of the general formula (I) in distilled water, containing sorbitol monooleate (0.02%) oxyethyleneated with ethylene oxide (about 20 mols).

Discs, 1 cm. in diameter, of leaves, are taken n days after the treatment and placed on agar inoculated with Erwinia chrysanthemi. 48 hours afterwards, the diameter (in mm.) of the inhibition aureoles formed around the disc is measured.

| Concentration of the suspension applied, in µg/cc. | Diameter (mm) of the inhibition aureole formed in contact with a disc taken n days after the treatment | | | |
| --- | --- | --- | --- | --- |
| | 0 | 1 | 6 | 14 |
| 250 | 19 | 19.5 | 14.2 | 10 |
| 125 | 16 | 16 | 10.5 | 0 |
| 62 | 10 | 11 | 0 | 0 |

Furthermore, other tests have shown that the phytotoxicity of the compound according to the invention, observed 10 days after the treatment, on wheat, on beans, on tomatoes and on cucumbers is zero at a concentration of 2,000 µg/cc.

Finally, open-air experiments carried out on pear trees have made it possible to establish the excellent activity of the compound according to the invention against Erwinia amylovora, responsible for fire blight.

These examples clearly show the remarkable bacteriostatic and bactericidal activities against numerous phytopathogenic strains, the good persistence of the activity, and the absence of phytotoxicity on the cultures. This compound can thus be used advantageously against diseases due to these bacteria and especially against fire blight caused by Erwinia amylovora on fruit trees and more particularly pear trees and apple trees.

For use in practice, the compound according to the invention is generally employed in association with at least one carrier or diluent and/or at least one surface-active agent compatible with the active material and suitable for use in agriculture. In these compositions, which also form part of the invention, the content of active material can be between 0.005% and 95% by weight.

The term "carrier" in the sense of the present description denotes an organic or inorganic, natural or synthetic material with which the active material is associated in order to facilitate its application to plants, to seeds or to the soil, or its transport or its handling. The carrier can be solid (clays, kaolin, bentonite, natural silicates, such as talc, or synthetic silicates, calcined magnesia, kieselguhr, tricalcium phosphate, cork powder, absorbent charcoal, resins, waxes, solid fertilisers and the like) or fluid (water, alcohols, ketones, petroleum fractions, chlorinated hydrocarbons, and liquefied gases).

The surface-active agent can be an emulsifier, dispersing agent or wetting agent, which can be ionic or non-ionic. Examples which may be mentioned are salts of polyacrylic acids, salts of ligninsulphonic acids, sulphoricinoleates, quaternary ammonium salts, condensates of ethylene oxide with fatty alcohols, fatty acids and fatty amines and especially the products based on ethylene oxide condensates such as the condensates of ethylene oxide with octylphenol, or esters of fatty acids and anhydro-sorbitols which have been solubilised by etherification of the free hydroxyl radicals by condensation with ethylene oxide. It is preferable to use agents of the non-ionic type, because they are not sensitive to electrolytes.

The compositions according to the invention can be prepared in the form of wettable powders, dusting powders, granules, solutions, emulsifiable concentrates, emulsions, suspension concentrates and aerosols.

The wettable powders according to the invention can be prepared, for example, by grinding the active material with the solid carrier, so that the powders contain from 20 to 95% by weight of the active material; they usually contain from 3 to 10% by weight of a dispersing agent and, where necessary, from 0 to 10% by weight of one or more stabilisers and/or other additives such as penetrating agents, adhesives or anti-caking agents, dyestuffs and the like.

By way of an example, the composition of a wettable powder is given below, the percentages being expressed by weight;

| | |
|---|---|
| Active material... compound of the formula I | 50% |
| Calcium lignosulphate (deflocculating agent) | 5% |
| Isopropylnaphthalenesulphonate (wetting agent) | 1% |
| Silica anti-caking agent | 5% |
| Kaolin filler | 39% |

The powders for the treatment of seed or for dusting are usually prepared in the form of a dust concentrate having a composition similar to that of a wettable powder, but without dispersing agent; they can be diluted on site by means of a supplementary amount of a fluid carrier, so that a composition is obtained with which the seeds to be treated can be coated conveniently, and which usually contains from 0.5 to 10% by weight of active material.

By way of example, the composition of a powder for the treatment of seed is given below:

| | |
|---|---|
| Active material compound of the formula I | 50% |
| Anionic wetting agent | 1% |
| Silica anti-caking agent | 6% |
| Kaolin (filler) | 43% |

The emulsifiable concentrates which can be applied by spraying after dilution with water usually contain the active material in solution in a solvent and, in addition to the solvent, and where necessary, a co-solvent, the solution containing from 10 to 50% by weight/volume of active material and from 2 to 20% by weight/volume of appropriate additives such as stabilisers, penetrating agents, corrosion inhibitors, dyestuffs and adhesives.

By way of example, the composition of an emulsifiable concentrate is given below, the amounts being expressed in g/liter.

| | |
|---|---|
| Active material compound of the formula I | 400 g/l |
| Dodecylbenzenesulphonate | 24 g/l |
| Nonylphenol oxyethyleneated with 10 molecules (of ethylene oxide) | 16 g/l |
| Cyclohexanone | 200 g/l |
| Aromatic solvent | c.s.p. 1 liter |

The concentrates in suspension, which can also be applied by spraying, are prepared in such a way that a stable fluid product is obtained, which does not sediment, and which usually contains from 10 to 75% by weight of active material, from 0.5 to 15% by weight of surface-active agents, from 0.1 to 10% by weight of anti-sedimentation agents such as protective colloids and thixotropic agents, and from 0 to 10% by weight of suitable additives, such as anti-foam agents, corrosion inhibitors, stabilisers, penetrating agents and adhesives and, as the carrier, water or an organic liquid in which the active material is substantially insoluble; certain organic solid materials or inorganic salts can be dissolved in the carrier to assist in preventing sedimentation, or as anti-freeze agents for the water.

Aqueous dispersions and emulsions, for example compositions obtained by diluting a wettable powder or an emulsifiable concentrate, according to the invention, with water, at the rate of 10 to 100 g. of active material per hectolitre of water, are included in the general scope of the present invention. These emulsions can be of the water-in-oil type or of the oil-in-water type and can have a thick consistency such as that of a "mayonnaise".

The compositions according to the invention can contain other ingredients, for example protective colloids, adhesives or thickeners, thixotropic agents, stabilisers and sequestering agents as well as other active materials which are known to have pesticidal properties, and particularly insecticides or fungicides.

It will be obvious to those skilled in the art that various changes may be made without departing from the scope of the invention and the invention is not to be considered limited to what is described in the specification.

What is claimed is:

1. A compound, of the formula:

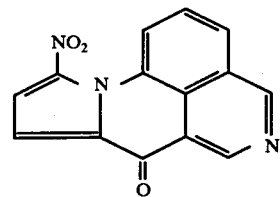

2. A process for the preparation of a product according to claim 1 comprising the step of nitrating a compound of the formula:

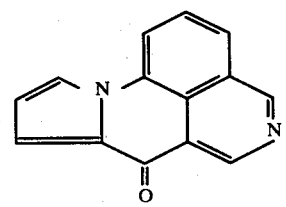

3. A process according to claim 2 wherein said nitrating agent is a solution of fuming nitric acid in trifluoromethanesulphonic acid.

4. A process in accordance with claim 3 wherein the reaction is carried out at a temperature of −10° C to −15° C.

5. An agricultural bactericide, comprising a bactericidally-effective amount of 10-nitro-7-oxo-7H-indolizino (7,6,5-de) isoquinoline, an inert agricultural carrier, and a compatible surface-active agent suitable for agricultural use.

6. A composition in accordance with claim 5 containing 0.005 to 95% by weight of said active compound.

7. A composition in accordance with claim 5, further comprising one or more other pesticides compatible with said active compound and with said carrier and said surface-active agent.

8. A process for the protection of plants against bacterial diseases, comprising applying a bactericidally-effective amount of the compound of claim 1 to said plants.

9. A process for the protection of plants against bacterial diseases, comprising applying a bactericidally-effective amount of the composition of claim 5 to said plants.

10. A process for combating fire blight in fruit trees, comprising applying to the leaves of said fruit trees as a spray or dust an amount sufficient of the compound of claim 1 to prevent said fruit trees from contracting fire blight.

* * * * *